United States Patent [19]

Likarova

[11] Patent Number: 5,224,989
[45] Date of Patent: Jul. 6, 1993

[54] FILM-FORMING DISPERSION FOR A PROTECTIVE COATING OF DRUG AND FOOD CONTAINING ARTICLES AND OBJECTS

[76] Inventor: Eva Likarova, 3826 Ross Rd., Palo Alto, Calif. 94303

[21] Appl. No.: 793,454

[22] Filed: Nov. 18, 1991

[51] Int. Cl.$^5$ ............................................. C08L 3/10
[52] U.S. Cl. .................................... 106/210; 106/181; 106/213; 106/214; 424/479; 426/103; 426/302; 426/661
[58] Field of Search ............... 106/181, 213, 214, 210; 424/479; 426/661, 302, 103

[56] References Cited

U.S. PATENT DOCUMENTS 3,408,214 10/1968 Mentzer ............................... 106/213
4,738,724 4/1988 Wittwer et al. ..................... 106/213

Primary Examiner—David Brunsman
Attorney, Agent, or Firm—Hana Dolezalova

[57] ABSTRACT

A film-forming dispersion for the formation of protective coatings on shaped drug and food articles which comprises 1 to 25 weight percent of acetylester of oxidized starch and 0.8 to 8 weight percent of triethylcitrate.

17 Claims, No Drawings

FILM-FORMING DISPERSION FOR A PROTECTIVE COATING OF DRUG AND FOOD CONTAINING ARTICLES AND OBJECTS

BACKGROUND OF THE INVENTION

1. Field of Invention

This invention relates to a film-forming dispersion useful for formation of a protective coating on shaped drug and food articles. In particular, this invention relates to a film-forming dispersion containing essentially acetylester of oxidized starch and triethylcitrate useful for surface protection of drug and food containing tablets, pellets, pills, granules or their components in crystalline form, especially those containing one or more active substances and ingredients.

2. Background Art and Related Art Disclosures

It is generally known that the drugs, medicaments, food supplements or food substitutes intended for oral administration, when molded into the final form, are often sensitive to physical and chemical effects of the environment, such as heat, light or humidity, all of which substantially decrease the shelf-life of the preparation. Moreover, many of these preparations have an unpleasant flavor properties. Also, in case of more than one active ingredient, undesirable chemical reactions may occur among the active components themselves or between an active component and an auxiliary component. For these reasons the final product or some of its active components should be protected by coating these components with protective films (layers) which would provide a barrier preventing detrimental inter-reactions between various components or decomposition of active ingredients by heat, light, humidity, etc. Such protection is usually achieved by coating these articles or components with solutions of various film-forming substances.

The oldest known method for surface protection of tablets, pellets, pills, granules, etc., is the pelletization where the surface of molded drug cores (uncoated tablets, pills, etc.) is covered with a thick layer of saccharose optionally containing also other auxiliary compounds including dyes.

Another type of surface protected drugs are so called core coated tablets whose active ingredient containing core is coated either with a thin layer of a cellulose derivative or with a suitable polymeric material. Most commonly used coating materials are cellulose derivative hydroxypropyl methylcellulose, and polymers acrylates and methacrylates. All of these film-forming solutions used for the core coating, however, are based on the presence of organic solvents or their mixtures. The protective film is formed on cores after the solvent evaporation, releasing said solvent into the atmosphere. Besides the environmental pollution, there is also a large loss of the organic solvents which has an economic impact. Further, the handling of organic solvents may endanger workers' health and is fire hazardous. However, for lack of better coating process, the method is widely used and effective equipments have been developed to produce these protective films containing hydropropyl methylcellulose and polymers in large quantities.

The primary disadvantage of these above described method of preparation of surface protected articles is the fact that the film-forming substances are soluble only in solutions containing organic solvents or their mixtures, both of which may leave residues in the article coating or be otherwise harmful to the patient or consumer. Thus, it would be extremely advantageous to have available coating which would allow the elimination of the use of organic solvents or their mixtures.

Previously, certain attempts were made to exclude from the technology of preparation of surface protected articles the film-forming solutions based on organic solvents and replace them by water based solutions or dispersions. For this purpose, some water-soluble cellulose derivatives, such as hydroxypropyl methylcellulose, commercially available from DOW Chemical as Methocel E5 and E15 or water dispersions of acrylate polymers, commercially available as Eudragit TM from RHOM PHARMA, Germany, were developed. The water cellulose, however, form very viscous solutions and therefore are not overly suitable for achieving the effective coating.

While possessing much better properties than organic solvents coatings, these film-forming water solutions and dispersions are not without shortcomings. For example, the disadvantage of hydroxypropyl methylcellulose used frequently for these dispersions is its viscosity. Because it forms rather viscous solutions, it can only be used in a concentration of up to 8%. The disadvantage of the water dispersions of the acrylate polymers, on the other hand, is their instability towards external effects of temperature, pressure and their incompatibility with other auxiliary compounds. Since it is not easy to rapidly remove the water from the water based film-forming solutions, the cores containing active ingredient are for a relatively long period of time in contact with water while being, at the same time, submitted to high temperatures and continuous aeration. This is especially so when working in fluid bed. Under these circumstances, the decomposition of the active substances can and does easily occur.

It would be, therefore, advantageous to have available a coating method which would avoid such long exposure of the active ingredient to the water, aeration, and high temperature and still achieve the same purpose, that is a long-term protection of the active ingredient containing core against excessive heat, humidity or light deterioration.

It is, therefore, a primary object of this invention to provide a film-forming dispersion which would effectively protect core containing active ingredient without submitting the core to undesirable contact with water for extended period of time as well as to high temperature, pressure, and aeration The current invention concerning a novel type of protective coating avoids all these undesirable exposures while resulting in effective, desirable, safe and economical protective coating for drug and food containing articles and objects.

SUMMARY

One aspect of this invention is a film-forming protective coating dispersion consisting essentially of acetylester of oxidized starch and triethylcitrate.

Another aspect of this invention is the film-forming dispersion wherein acetylester of oxidized starch containing from 0.5 to 2.4 weigh percent of bonded acetyl is present in the dispersion in amount from 1-25 weight percent together with 0.8-8 weight percent of triethylcitrate.

Still another aspect of this invention is the film-forming dispersion is prepared by dissolving of acetylester of the oxidized starch in demineralized water, heating the suspension to the temperature of 85° to 90° C. under constant stirring cooling the suspension cools down to about 40° C. and adding triethylcitrate and another auxiliary compounds.

Yet another aspect of the current invention is a coating of cores containing active ingredient by spraying the dispersion on the cores in a suitable coating equipment.

Still yet another aspect of this invention is the protection of cores containing active ingredients formed into shaped objects such as tablets, pellets, pills or granules from destructive efforts of heat, humidity or light or from unwanted inter-reactions among individual active components.

DETAILED DESCRIPTION OF THE INVENTION

The current invention concerns an improved film-forming dispersion for protection of drug and food articles and objects by coating these articles and objects with easily dissolvable surface coating.

A film-forming dispersion for the forming of a protection layer on shaped drug and food articles and objects such as tablets, pills, granules and pellets or on their individual components in crystalline form consists, according to the invention, of to 25 weight percent, preferably 8 to 15 weight percent of the acetylester of oxidized starch and of 0.8 to 8 weight percent, preferably 3.5 to 6 weight percent, of triethylcitrate dissolved in water up to 100 weight percent. Acetylester of oxidized starch preferably contains from 0.5 to 2.4 weight percent of bonded acetyl. The dispersion can further contain softening agents, binding agents, fillers such as sodium carboxymethylcellulose, talcum, titanium dioxide and macrogels. The film-forming dispersion can thus optionally contain 0.1 to 0.5 weight percent of sodium carboxymethylcellulose, and talcum, titanium dioxide, polyethylene glycol having a molecular weight of about 300 to 15000 in amount of 0.03 to 10 weight percent, water-soluble dyes and pigments, aromatic correction additives, taste enhancers and other additives known in the pharmaceutical sciences which are pharmaceutically suitable and acceptable.

The primary embodiment of the film-forming dispersion, according to the invention, is prepared by mixing the acetylester of the oxidized starch in amount from 1 to 25 wt/%, preferably in amount 8–15 wt/%, in demineralized water. The suspension is then slowly heated up to 85 to 90° C. under constant stirring. When all acetylester is dissolved, the solution is cooled to about 40° C., and 0.8 to 8 wt%, preferably 3.5 to 6 wt%, of triethylcitrate is added. If desirable, further auxiliary compounds are also added at this time.

Any of the above suspension mixture is homogenized for 15–60 minutes, preferably for 20 minutes in a colloidal mill under room temperature. The obtained homogenized dispersion is immediately usable for spraying on the preprepared cores containing active ingredient in any suitable type of coating equipment such as, for example, Accela Cota commercially available from Manesty, Great Britain or Glatt Coater, from Glatt, Switzerland, at input temperature from 36–60° C., preferably at 45° C. and at output temperatures of 30–40° C. preferably 37° C.

Film-forming dispersion according to the invention has a very low viscosity and it can therefore, be used as 30% dispersion. The low viscosity allows a higher amount of fillers and auxiliary compounds to be used to make the dispersion more concentrated. This significantly cuts down the time needed for the spraying as well as the time when the active components are exposed to water which could lower the effectivity of the formulated drugs or medicament tablets.

Moreover, because of the low viscosity, another ingredients could be easily added to the film-forming dispersion suspension. In this way, the otherwise incompatible components could be combined together to form the coating dispersion having better protection properties.

The invention is further advantageously applicable for coating of several active ingredients which need to be formulated together to provide a more effective drug, medicament, food supplement or substitute. If, for example, two or more incompatible active ingredients need to be formulated in one tablet, they can be separately precoated with film-forming dispersion of the current invention, then formulated into final shaped article or object, and again coated with appropriate film-forming dispersion containing for example different additives, such as taste enhancers, than those used for the coating of the individual active ingredients. These and other similar combinations are intended to be encompassed within the scope of this invention.

The film-forming dispersion of the current invention has many advantages over the coating method currently used using hydroxypropyl methylcellulose such as Methocel E5, Methocel E15 or Pharmacoat.

Film-forming dispersions according to the invention can be prepared right before the actual spraying. Warming the dispersion to the temperature of 90° C. and continuous stirring enables fast dissolving of the suspension. The high temperature stabilities the suspension microbiologically. The prior suspensions using hydroxypropyl methylcellulose must be prepared at least 12 hours before the actual spraying because such suspensions cannot be stirred, as the stirring would damage the polymer chains. Thus, the entire dissolution of these prior suspensions lasts much longer. This increases a chance of bacterial growth and in general lengthens the processing.

In testing the current invention, the properties of the biodegradable film-forming material according to the invention were compared with those of the films based on hydroxypropyl methylcellulose (Methocel E5 or E15). Hydroxypropyl methylcellulose has a high viscosity and could be only used as 8 percent solution. The hydroxypropyl methylcellulose suspension having higher concentration was too dense for spraying. Since the larger amount of water was needed to solubilize hydroxypropyl methylcellulose, the removal of this water almost doubled the spraying time and drug exposure to water. The results of dissolution tests of tablets coated with the current dispersion or with hydroxypropyl methylcellulose were by 10 to 15% better with the films according to the current invention than with films based on hydroxypropyl methylcellulose. For these testings, both the current film-forming dispersion and the hydroxypropyl methylcellulose method, were used to coat Ibuprofen tablets. These coated tablets were tested for the dissolution and for the release of the active substances from the coated tablets. Tests proved that the Ibuprofen tablets coated with the film-forming dispersion according to the invention were dissolved and the whole amount, i.e. approximately 100% of the active ingredient, was released in about 30 minutes. The tablets coated with hydroxypropyl methylcellulose film dissolved in approximately 50 minutes and, at that time, only about 80 percent of active substance was released.

UTILITY

The film-forming dispersion according to the invention are useful for protective coating of shaped articles and objects, such as drugs, medicaments, food supplements or food substitutes containing tablets, pills, pellets, granules or otherwise shaped objects. The invention is particularly useful and has the best impact on protection of the articles and objects where the active components need to be released immediately after administration to speed up the therapeutic effect. Such fast release is needed for all pain relievers, fever reducers, arthritis drugs, digesting disorder relievers, vitamins, etc.

On other hand, the dispersions of the current invention are very useful for providing protective coating for drugs, medicines, food supplements or substitutes where such drugs and medicaments are bitter, sour, salty or have objectionable smell or taste. Thus, these coatings prevent a maltasting effect of components with unpleasant taste such as, for example, chinin sulfate, ibuprofen, or ascorbic acid. The taste of the basic protective coating may be enhanced by adding other ingredients such as fruit powder, dextrose, fructose, and other natural and artificial flavors and food colors suitable for human consumption.

In veterinary medicine, these tablets, pills, granules or pellets may be similarly coated with dispersion containing artificial meat or milk flavor or some other attractants and lurants to make the drug or medicine more tasteful for treated animal.

The other, no less important utility for film forming dispersions of the current invention is the protection of active ingredients from harmful external effects such from the effect of light, temperature, humidity, etc. Such protection effectively extends the shelf-life of the product and has thus important economic effect.

The film-forming coating according to this invention is easy, fast, and inexpensive. All components used in the current suspension are commonly available, low cost chemicals often used in the pharmaceutical industry. Overall, film-forming dispersions according to the invention are significantly cheaper than when hydroxypropyl methylcellulose is used.

The invention is further illustrated in the following examples. These examples are not intended to limit the scope of the invention in any way.

EXAMPLE 1

Preparation of Acetylated Starch Coating

Acetylated starch in an amount of 15 kg was dissolved in 145 kg demineralized water and heated to 85° to 90° C. under continuous stirring. After that, 3.75 kg of triethycitrate, 7.8 kg of talcum and 3.3. kg of pigment were added. The suspension was homogenized in a colloidal mill for 20 minutes. The dispersion was then sprayed on the cores in a coating equipment Accela Cota, at an input temperature of 48° to 44° C. and an output temperature of 38 to 36° C.

The resulting film was elastic and did not slow the drug release from the core.

EXAMPLE 2

Preparation of Acetylated Starch-Sodium Carboxy-methylcellulose Coating

A 6.7 kg of acetylated starch was dissolved in 52.8 kg of demineralized water. The suspension was continuously stirred and heated up to about 85° to 90° C. After that, 1.5 kg of triethylcitrate, 0.1 kg of sodium carboxymethyl cellulose, 2.5 kg of talc and 0.8 kg of a pigment were added. The suspension was homogenized in a colloidal mill for 20 minutes and then sprayed on uncoated tablets. The results were the same as in Example 1.

EXAMPLE 3

Preparation of Acetylated Starch-Polyethylene Glycol Containing Coating

In 135 kg of demineralized water 14.4 kg of the acetyl derivative of starch was dissolved. The suspension is heated to the temperature of 85° to 90° C. and constantly stirred. Then 2.5 kg of triethyl-citrate, 0.8 kg of polyethylene glycol with molecular weight of 6,000, 3.65 kg of talcum, and 1.5 kg of titanium dioxide were added. The suspension was homogenized in a colloidal mill for 20 minutes. Glatt Coater coating machine was used for spraying. The temperature wa kept at 40° C. during the spraying.

The effect was the same as in Example 1.

What is claimed is:

1. A film-forming dispersion for the formation of a protective coating on shaped drug and food articles and objects or their components in crystalline form said dispersion consisting essentially of 1–25% by weight of acetylester of oxidized starch containing from 0.5 to 2.4% by weight of bonded acetyl and 0.8 to 8% by weight of triethylcitrate.

2. The dispersion of claim 1 further containing 0.1 to 0.5% by weight of sodium carboxymethylcellulose.

3. The dispersion of claim 2 wherein the said dispersion contains from 8 to 15% by weight of the acetylester of oxidized starch.

4. The dispersion of claim 3 wherein the said dispersion contains from 3.5 to 6% by weight of triethylcitrate.

5. The dispersion of claim 4 wherein said dispersion further contain 0.03 to 10% by weight of polyethylene glycol with molecular weight of about 300 to 15,000.

6. The dispersion of claim 5 wherein the said dispersion contains from 8 to 15% by weight of the acetylester of oxidized starch.

7. The dispersion of claim 6 additionally containing between 0.03–10% by weight of talcum.

8. The dispersion of claim 7 additionally containing 0.03–2% by weight of titanium dioxide with proviso that the cumulative amount of talcum and titanium dioxide does not exceed 10%.

9. The film-forming dispersion of claim 8 wherein the said dispersion contains water soluble dyes or pigments.

10. A film-forming dispersion for the formation of a protective coating on shaped drug and food articles and objects consisting of 1 to 25% by weight of acetylester of oxidized starch, 0.8–8% by weight of triethylcitrate and 0.1 to 0.5% by weight of sodium carboxymethylcellulose in water up to 100% by weight.

11. The dispersion of claim 10 wherein the said dispersion contains 8 to 15% by weight of the acetyl ester of oxidized starch and 3.5 to 6% by weight of triethylcitrate.

12. The dispersion of claim 11 additionally containing between 0.03–10% by weight of talcum.

13. The dispersion of claim 12 additionally containing 0.03–2% of titanium dioxide with proviso that the cumulative amount of talcum and titanium dioxide does not exceed 10%.

14. A film-forming dispersion for the formation of a protective coating on shaped drug and food articles and objects consisting of 1 to 25% by weight acetylester of oxidized starch, 0.8 to 8% by weight of triethylcitrate and, 0.03 to 10% by weight and polyethylene glycol with a molecular weight of about 300 to 15000.

15. The dispersion of claim 14 wherein the said dispersion contains 8 to 15% by weight of the acetyl ester of oxidized starch and 3.5 to 6% by weight of triethylcitrate.

16. The dispersion of claim 15 additionally containing between 0.03–10% by weight of talcum.

17. The dispersion of claim 16 additionally containing 0.03–2% of titanium dioxide with proviso that the cumulative amount of talcum and titanium dioxide does not exceed 10 percent.

* * * * *